(12) United States Patent
Kim et al.

(10) Patent No.: US 11,278,249 B2
(45) Date of Patent: Mar. 22, 2022

(54) INTRAORAL SENSOR AND X-RAY IMAGING SYSTEM USING THE SAME

(71) Applicants: Rayence Co., Ltd., Gyeonggi-do (KR); VATECH EWOO Holdings Co., Ltd., Gyeonggi-do (KR)

(72) Inventors: Tae Woo Kim, Gyeonggi-do (KR); Yu Sung Jeon, Gyeonggi-do (KR); Yeong Kyun Kim, Gyeonggi-do (KR); Jung Do Kim, Gyeonggi-do (KR)

(73) Assignees: RAYENCE Co., Ltd., Gyeonggi-do (KR); VATECH EWOO Holdings Co., Ltd., Gyeonggi-do (KR)

( * ) Notice: Subject to any disclaimer, the term of this patent is extended or adjusted under 35 U.S.C. 154(b) by 122 days.

(21) Appl. No.: 15/921,972

(22) Filed: Mar. 15, 2018

(65) Prior Publication Data
US 2018/0263580 A1   Sep. 20, 2018

(30) Foreign Application Priority Data

Mar. 15, 2017  (KR) .................. 10-2017-0032536
Sep. 20, 2017  (KR) .................. 10-2017-0121218

(51) Int. Cl.
| | | |
|---|---|---|
| *A61B 6/14* | (2006.01) | |
| *G01T 1/208* | (2006.01) | |
| *G01T 7/00* | (2006.01) | |
| *G01T 1/24* | (2006.01) | |
| *H04N 5/32* | (2006.01) | |

(52) U.S. Cl.
CPC ............. *A61B 6/145* (2013.01); *G01T 1/208* (2013.01); *G01T 1/244* (2013.01); *G01T 7/00* (2013.01); *H04N 5/32* (2013.01)

(58) Field of Classification Search
CPC .. A61B 6/00; A61B 6/14; A61B 6/145; A61B 6/42; A61B 6/4208; A61B 6/425; A61B 6/4275; G01N 2800/18; G01N 23/083; G01N 23/06; G01N 23/02
See application file for complete search history.

(56) References Cited

U.S. PATENT DOCUMENTS 6,030,119 A *  2/2000  Tachibana .............. A61B 6/145
                                                            378/169
9,602,639 B2 *  3/2017  Carnevali ............ H04M 1/0274
(Continued)

FOREIGN PATENT DOCUMENTS

JP     2011-120925 A    6/2011
KR  10-2014-0109810 A    9/2014
(Continued)

*Primary Examiner* — David P Porta
*Assistant Examiner* — Mamadou Faye
(74) *Attorney, Agent, or Firm* — IP Legal Services, LLC

(57) ABSTRACT

Disclosed are an intraoral sensor and an X-ray imaging system. The intraoral sensor includes a sensor panel, a circuit unit, a memory, a battery, a casing, a first connector, and a power terminal. The X-ray imaging system includes a docking station with the intraoral sensor docked thereto, the docking station configured to provide a second connector connected to the first connector to perform at least one function of receiving the image signal stored in the memory, and charging the battery, or includes a transmission cable detachably connected to the intraoral sensor, and configured to provide a third connector connected to the first connector to transmit the image signal.

15 Claims, 10 Drawing Sheets

(56) References Cited

U.S. PATENT DOCUMENTS

| | | | |
|---|---|---|---|
| 2001/0045904 A1* | 11/2001 | Silzer, Jr. ............... | H04W 4/021 |
| | | | 342/357.57 |
| 2001/0055368 A1* | 12/2001 | Carroll ..................... | A61B 6/14 |
| | | | 378/189 |
| 2004/0065836 A1 | 4/2004 | Schick et al. | |
| 2004/0065837 A1 | 4/2004 | Schick et al. | |
| 2004/0066898 A1 | 4/2004 | Schick et al. | |
| 2006/0193436 A1 | 8/2006 | Schick et al. | |
| 2012/0330556 A1* | 12/2012 | Shaanan ............ | A61B 5/15087 |
| | | | 702/19 |
| 2013/0346661 A1* | 12/2013 | Hasenei ................ | G06F 1/1632 |
| | | | 710/303 |
| 2014/0254756 A1 | 9/2014 | Tagawa | |
| 2015/0111398 A1* | 4/2015 | Isenhour .............. | G02B 6/3886 |
| | | | 439/39 |
| 2017/0086760 A1 | 3/2017 | Kim et al. | |
| 2017/0162990 A1* | 6/2017 | Wu ........................ | H01R 31/06 |
| 2018/0160991 A1 | 6/2018 | Chun et al. | |

FOREIGN PATENT DOCUMENTS

| | | |
|---|---|---|
| KR | 10-2015-0109835 A | 10/2015 |
| KR | 10-2016-0066373 A | 6/2016 |
| KR | 10-2016-0134701 A | 11/2016 |
| KR | 10-1695404 B1 | 1/2017 |

\* cited by examiner

INTRAORAL SENSOR AND X-RAY IMAGING SYSTEM USING THE SAME

CROSS REFERENCE TO RELATED APPLICATION

The present application claims priority to Korean Patent Application No. 10-2017-0032536, filed Mar. 15, 2017, and No. 10-2017-0121218, filed Sep. 20, 2017, the entire contents of which is incorporated herein for all purposes by this reference.

BACKGROUND OF THE INVENTION

Field of the Invention

The present invention relates to an intraoral sensor and an X-ray imaging system using the same.

Description of the Related Art

Recently, digital intraoral sensors have been used to obtain X-ray images of teeth and surrounding tissues in an oral cavity.

In a conventional X-ray imaging system using an intraoral sensor, X-ray imaging is performed using a cable-type intraoral sensor to which a transmission cable is fixed and connected, and an image signal generated from the intraoral sensor by X-ray imaging is transmitted to a diagnostic computer via the transmission cable.

As described above, the conventional X-ray imaging is problematic in that since a cable-type intraoral sensor is used, there are various limitations in intraoral X-ray imaging, such as reduced convenience, breakage of the transmission cable, or connection failure.

SUMMARY OF THE INVENTION

Accordingly, the present invention has been made to overcome the limitation due to use of the conventional cable-type intraoral sensor.

In order to achieve the above object, there is provided an intraoral sensor including: a sensor panel configured to generate an image signal by X-ray imaging; a circuit unit provided with a driver circuit configured to drive the sensor panel; a memory configured to store the image signal; a battery configured to supply driving power to the sensor panel and the circuit unit; a casing configured to accommodate the sensor panel, the circuit unit, the memory, and the battery; a first connector exposed to outside of the casing and configured to include at least one of a signal transmission terminal transmitting the image signal, and a power terminal supplying power to the battery; and a protrusion configured to protrude backward from the intraoral sensor and provided with the first connector at a side thereof.

In order to achieve the above object, there is further provided an X-ray imaging system including: the intraoral sensor aforementioned; and a docking station with the intraoral sensor docked thereto, the docking station configured to provide a second connector connected to the first connector receiving the image signal stored in the memory, or charging the battery.

In order to achieve the above object, there is further provided an X-ray imaging system including: the intraoral sensor aforementioned; and a transmission cable detachably connected to the intraoral sensor, and configured to provide a third connector connected to the first connector to transmit the image signal.

According to the present invention, the cableless intraoral sensor provided with the battery and the memory therein may be used. Further, by using the docking station to which the intraoral sensor is docked, or the transmission cable detachably connected to the intraoral sensor, it is possible to transmit an image signal generated from the intraoral sensor to the computer.

Accordingly, the convenience of intraoral X-ray imaging can be maximized, and breakage of the transmission cable or connection failure can be fundamentally eliminated, whereby it is possible to effectively improve the limitation of intraoral X-ray imaging due to use of a conventional cable-type intraoral sensor.

Further, in connecting the intraoral sensor to the docking station or transmission cable, the corresponding connectors are connected by using magnetic force.

Thereby, the erroneous connection between the connection terminals of the connectors may be reduced, thereby ensuring the connection stability between the connectors.

BRIEF DESCRIPTION OF THE DRAWINGS

The above and other objects, features and other advantages of the present invention will be more clearly understood from the following detailed description when taken in conjunction with the accompanying drawings, in which.

DETAILED DESCRIPTION OF THE INVENTION

Hereinbelow, the present invention will be described in more detail with reference to the accompanying drawings.

For reference, an X-ray imaging system including an intraoral sensor according to the present invention can be divided into several embodiments for convenience, and in the following, each embodiment is described separately and the common content is explained through the first embodiment.

First Embodiment

Figure 1:
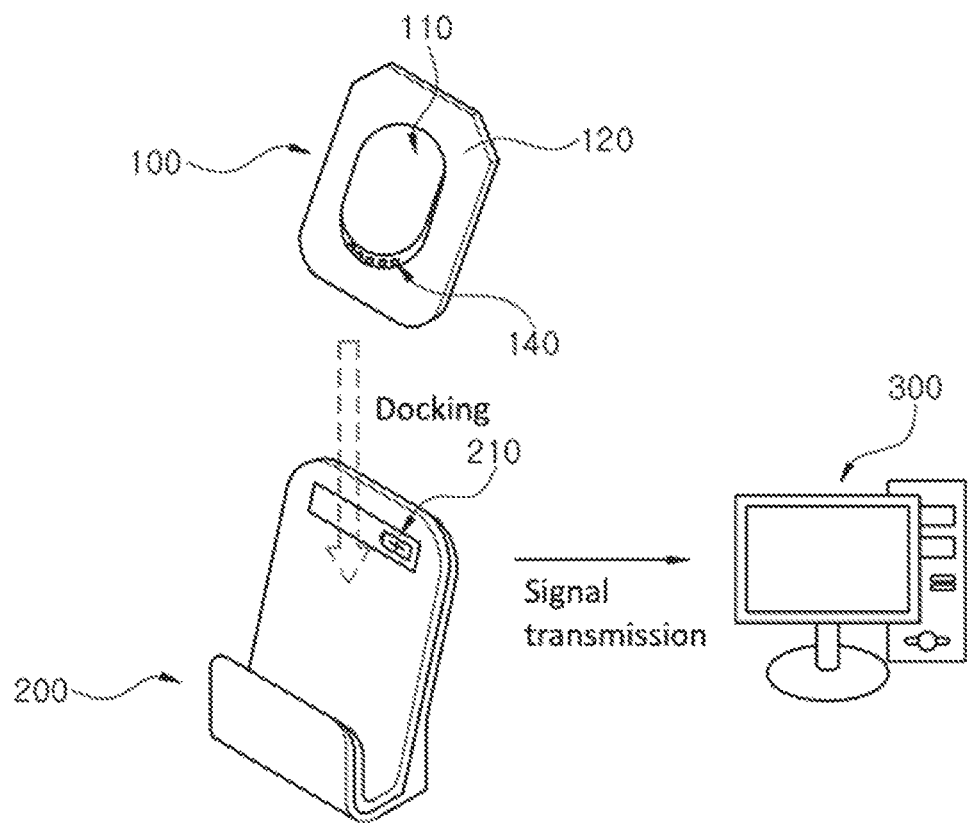
FIG. 1 is a view schematically showing an X-ray imaging system including an intraoral sensor according to a first embodiment of the present invention.

FIG. 1 is a view schematically showing an X-ray imaging system including an intraoral sensor according to a first embodiment of the present invention.

An X-ray imaging system 10 according to the first embodiment of the present invention may include an intraoral sensor 100, a docking station 200, and a diagnostic computer 300.

The computer 300 can display an X-ray image by receiving and processing an image signal generated from the intraoral sensor 100 during X-ray imaging.

The intraoral sensor 100 is inserted into an oral cavity to perform X-ray detection on teeth and surrounding tissues. To achieve this, the intraoral sensor 100 being inserted into the oral cavity detects X-rays that are generated by an external X-ray generator and transmitted through the teeth and the surrounding tissues, and generates electrical signals according to X-ray intensity by position.

The intraoral sensor 100 may be a direct type X-ray sensor that directly converts X-rays into electrical signals, or an indirect type X-ray sensor that converts X-rays into visible light and then converts the visible light into electrical signals.

Particularly, the intraoral sensor 100 of the embodiment is a cableless intraoral sensor 100 without a separate transmission cable, so the intraoral sensor 100 can perform intraoral X-ray imaging in an independent state without a separate transmission cable connection.

Figure 2:
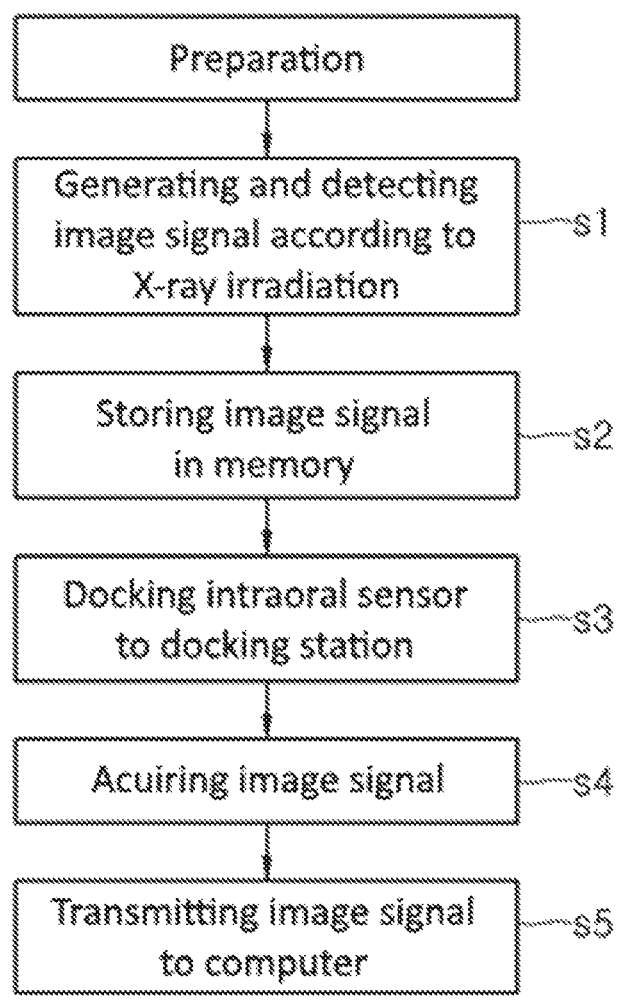
FIG. 2 is a flowchart showing an image signal transmission method of the X-ray imaging system including the intraoral sensor according to the present invention.

To be specific to the internal configuration of the intraoral sensor 100 with reference to FIG. 2, the intraoral sensor 100 may include a sensor panel 102, a circuit unit 104, a memory 106, and a battery 108.

The sensor panel 102 corresponds to a configuration for generating an image signal according to irradiated X-rays, which is arranged in a matrix form, and may include a plurality of pixels that generates and outputs a corresponding image signal. Meanwhile, in the case of the indirect type, a scintillator may be provided on a front surface of the sensor panel 102, which is an X-ray incident surface, as a phosphor that converts X-rays to visible light.

The circuit unit 104 may be disposed on a rear surface of the sensor panel 102, which is the opposite side of the X-ray incident surface, wherein the circuit unit 104 may include at least one printed circuit board on which driver circuits for driving the sensor panel 102 are mounted. For example, a timing controller for generating a timing signal and processing and outputting an image signal may be mounted on the circuit unit 104, and a readout circuit for detecting the image signal generated from the sensor panel 102 may be mounted on the circuit unit.

The memory 106 stores the image signal detected through the lead-out circuit of the circuit unit 104, which is generated in the sensor panel 102 during X-ray imaging using the intraoral sensor 100 in a cable-less state. Here, the memory 106 may have a storage capacity capable of storing a plurality of X-ray images. In other words, the memory may have a capacity to store image signals corresponding to a plurality of frame images generated according to a plurality of X-ray shots.

The memory 106 may be provided and arranged separately from the circuit unit 104, and the memory 106 may be, for example, in the form of a thin film and may be disposed at behind the circuit unit 104. As another example, the memory 106 may be configured to be mounted on the circuit unit 104.

The battery 108 supplies power for operating the intraoral sensor 100 in a cable-less state. For example, it can provide driving power to the sensor panel 102, the circuit unit 104, and the memory 106. The battery 108 is a rechargeable secondary battery, and preferably, is in the form of a thin plate, and may be disposed behind the circuit unit 104, for example, behind the memory 106.

As described above, the intraoral sensor 100 is provided therein with the memory 106 and the battery 108 so that intraoral X-ray imaging can be performed in a cable-less state in which no transmission cable is used.

Meanwhile, the intraoral sensor 100 may include a first casing 120 that surrounds the sensor panel 102, the circuit unit 104, the memory 106, and the battery 108 to accommodate and protect the same from the outside.

Further, the intraoral sensor 100 may be provided with a protrusion 110 protruding backward from the rear side opposite to the incident side of the X-rays. The protrusion 110 can function as a sensor holder, which is a separate instrument for the user to hold by hand or align the intraoral sensor 100 with the X-ray generator, or a gripper to which an XCP (extension cone paralleling instrument) is fastened.

Meanwhile, the intraoral sensor 100 may be provided with a soft mold surrounding an outer surface thereof. For example, the soft mold may be configured to surround the first casing 120 and the protrusion 110.

Further, a first connector 140 including a plurality of first connection terminals exposed to the outside may be provided on a side surface of the protrusion 110. The first connector 140 may include at least one signal transmission terminal for transmitting and receiving signals between the intraoral sensor 100 and the docking station 200 of external configuration. The signal transmission terminal is connected to at least one of the memory 106, and transmits the image signal stored in the memory 106 or transmits a predetermined control signal to the circuit unit 104.

Furthermore, the first connector 140 may include a power terminal that is supplied with power for charging the battery 108, and the power terminal is connected to the battery 108 of the intraoral sensor 100.

Here, to correspond to the first connector 140 of the intraoral sensor 100, the docking station 200 may be provided with a second connector (not shown).

In this case, when the intraoral sensor 100 is docked to the docking station 200 and is put thereon, the first connector 140 of the intraoral sensor 100 contacting the second connector of the docking station 200. In this connection state, an image signal, a control signal, and the like can be transmitted between the intraoral sensor 100 and the docking station 200 through the signal transmission terminal, and the battery 108 can be charged with power from the docking station 200 through the power terminal. Here, for power supply, the docking station 200 may be provided therein with a separate battery or may be wired to an external power source.

The docking station 200 corresponds to a structure to which the intraoral sensor 100 is docked/undocked.

When the intraoral sensor 100 is docked, the docking station 200 may receive an image signal from the intraoral sensor 100 and transmit the transmitted image signal to the computer 300 in a wired or wireless manner. As such, the docking station 200 can perform a function of relaying the signal transmission between the intraoral sensor 100 and the computer 300.

The docking station 200 may be provided with a memory configured to store the image signal transmitted from the intraoral sensor 100.

Further, the docking station 200 may supply power to the intraoral sensor 100 in the docked state of the intraoral sensor 100 to charge the battery 108 of the intraoral sensor 100.

For image signal transmission and power supply, as described above, the docking station 200 may be provided with the second connector connected to the first connector 140 of the intraoral sensor 100 and exposed to the outside.

Further, the docking station 200 may be provided with a display window 210. The display window 210 may display information related to the intraoral sensor 100, for example, a state of the intraoral sensor 100 and a transmission state of the image signal.

Herein, with respect to the display of the state of the intraoral sensor 100, for example, the charging state of the battery 108, the total capacity or the used capacity or the remaining capacity of the memory 106, and the remaining life of the intraoral sensor 100 may be displayed. Here, instead of the total capacity or the used capacity or the remaining capacity of the memory 106, as the information having substantially the same meaning, the number of X-ray imaging operations (that is, the number of X-ray shots), the number of remaining shots, or the number of stored images or the number of remaining images may be displayed.

Further, with respect to the display of the transmission state of the image signal, for example, a signal transmission state from the intraoral sensor 100 to the docking station 200, a signal transmission state from the docking station 200 to the computer 300, and the like may be displayed.

Since the display window 210 is provided in the docking station 200, it is advantageous in that an operator can easily check the state of the intraoral sensor 100 and the signal transmission state.

Figure 3:
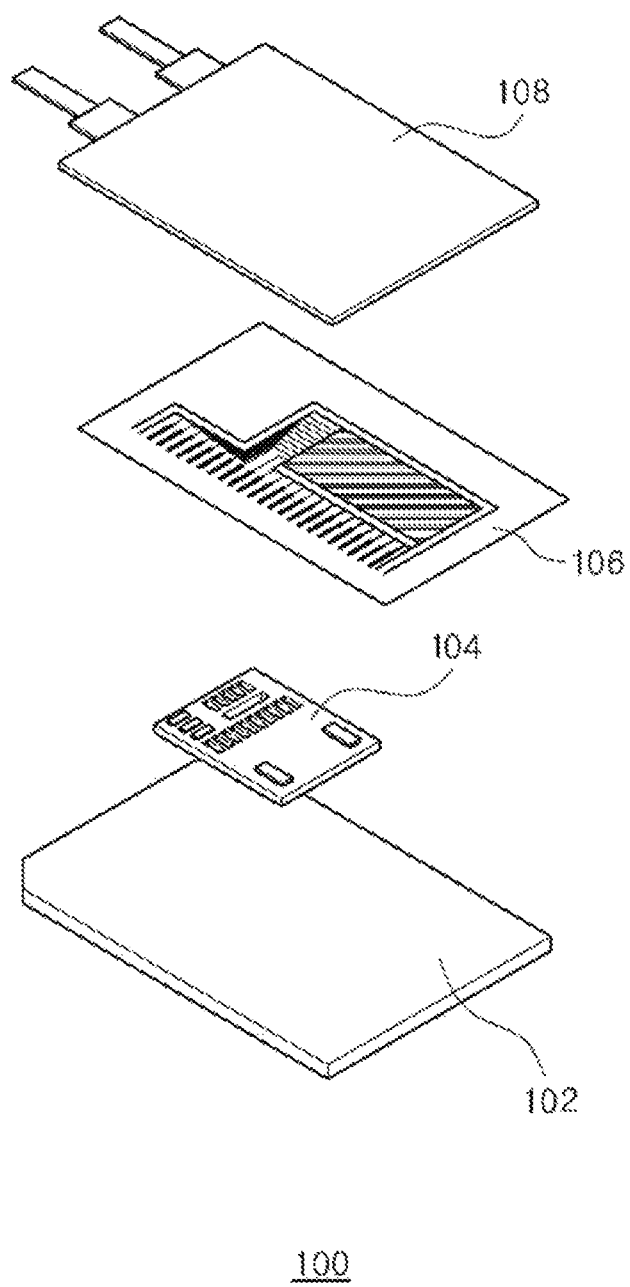
FIG. 3 is a view schematically showing a part of the intraoral sensor according to the present invention.

Hereinafter, an image signal transmission method according to an embodiment of the present invention will be described with reference to FIG. 3.

After the preparation step, an image signal is generated and detected by the intraoral sensor 100 according to X-ray irradiation (s1). In other words, intraoral X-ray imaging is performed.

Next, the detected image signal is stored in the memory 106 of the intraoral sensor 100 (s2). Here, depending on the storage capacity of the memory 106, s1 and s2 may be repeated several times.

Next, after X-ray imaging is finished, the intraoral sensor 100 is docked to the docking station 200 (s3).

Next, the docking station 200 acquires an image signal stored in the intraoral sensor 100 (s4). Here, the docking station 200 can charge the battery 108 of the intraoral sensor 100 and the acquired image signal can be stored in the memory provided in the docking station 200.

Next, the docking station 200 transmits the acquired image signal to the computer 300 (s5).

When the above process is completed, the intraoral sensor 100 is separated from the docking station 200.

Figure 4:
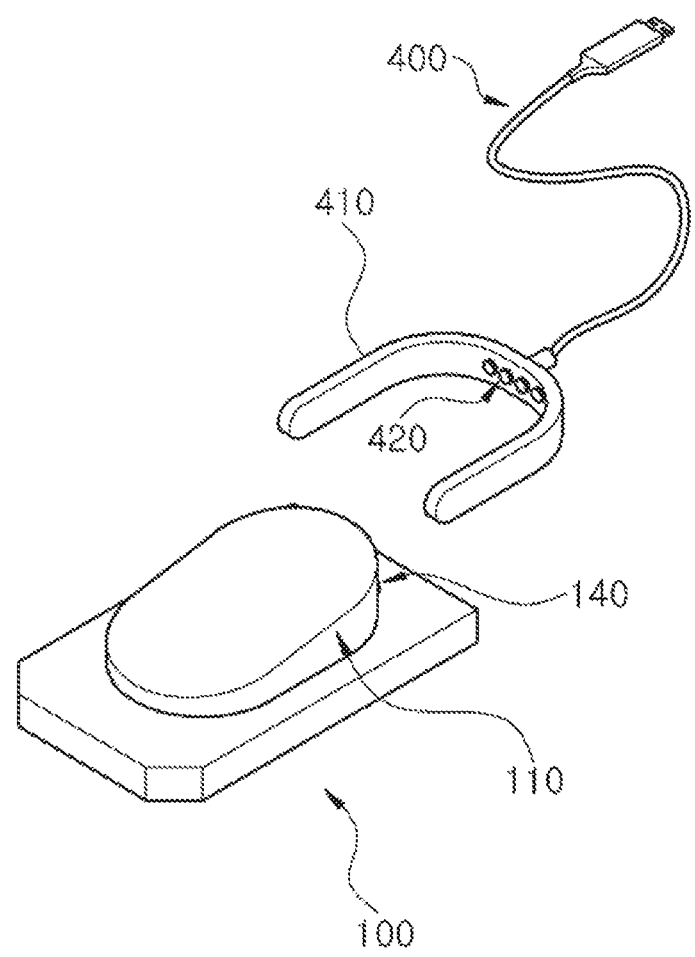
FIG. 4 is a view showing the intraoral sensor and a transmission cable detachably connected thereto according to the first embodiment of the present invention.

Meanwhile, the intraoral sensor 100 may be configured to be connected directly to the external computer 300 upon cable connection via a detachable transmission cable, and reference can be made to FIG. 4 in this regard.

FIG. 4 is a view showing a use of a transmission cable detachably connected to the intraoral sensor according to the first embodiment of the present invention.

An end of a transmission cable 400 may be provided with a coupler 410 configured to be coupled to or separated from the protrusion 110 of the intraoral sensor 100, and an inner surface of the coupler 410 may be provided with a third connector 420 including a third connection terminals connected to the first connector 140 of the intraoral sensor 100. Here, preferably, the coupler 410 is in the form of a ring that is open at one side to surround a portion of the side of the protrusion 110.

In this case, the protrusion 110 of the intraoral sensor 100 is inserted into the coupler 410 through the open side of the coupler 410, whereby the intraoral sensor 100 and the transmission cable 400 are coupled to each other, and the first connector 140 of the intraoral sensor 100 and the third connector 420 of the transmission cable 400 are brought into contact with each other.

In such a coupled state, the image signal stored in the memory 106 of the intraoral sensor 100 may be transmitted to the computer 300 connected thereto via the transmission cable 400. Further, the battery 108 of the intraoral sensor 100 can be charged through the power supplied from the computer 300.

As such, the image signal stored in the intraoral sensor 100 can be transmitted to the computer 300 as needed using the detachable transmission cable 400 instead of the docking station 200.

Meanwhile, in some cases, the intraoral sensor 100 with the transmission cable 400 coupled thereto may be inserted into the oral cavity to perform X-ray imaging, and in this case, the image signal generated in the intraoral sensor 100 can be transmitted to the computer 300 through the transmission cable 400.

Second Embodiment

Figure 5:
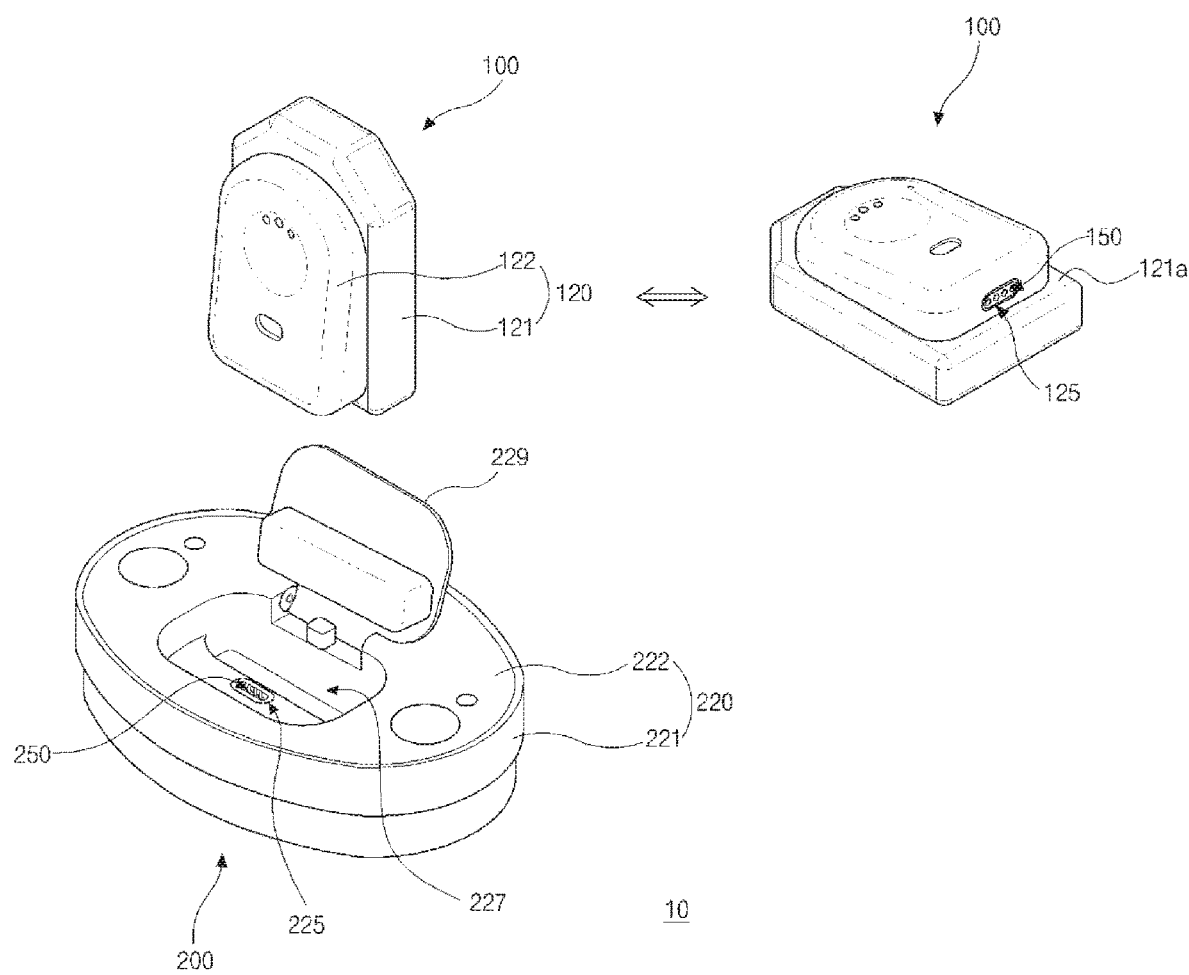
FIG. 5 is a view schematically showing an X-ray imaging system including an intraoral sensor according to a second embodiment of the present invention.

FIG. 5 is a view schematically showing an X-ray imaging system including an intraoral sensor according to a second embodiment of the present invention.

The first casing 120 of the intraoral sensor 100 according to the embodiment may include a first cover 121, which is a front cover placed forward on the incident surface side of the intraoral sensor 100, and a second cover 122, which is a rear cover placed backward on the opposite side of the incident surface. In this case, the electrical components of the intraoral sensor 100 can be accommodated in a receiving space inside the coupled first and second covers 121 and 122.

Further, the intraoral sensor 100 may have a shape in which a part or entire of the rear portion thereof protrudes rearward. For example, the second cover 122 may be formed in a protruding shape. As such, in the case where the intraoral sensor 100 is configured in a protruding shape, when the intraoral sensor 100 is viewed in cross section, the side surface of the intraoral sensor 100 has a stepped shape, that is, the front portion more protrudes outwardly than the rear portion.

Further, the intraoral sensor 100 may be provided with a first connector 150 including a first connection terminal for signal transmission to the outside or power supply for charging.

Herein, the first connector 150 may be accommodated in the first casing 120, and may be configured such that an end of the first connector 150 is exposed through a first connector hole 125 formed in the first casing 120.

The docking station 200 may be provided with a second casing 220 configured to accommodate internal components, and the second casing 220 may include a third cover 221, which is a lower cover placed at the bottom surface, and a fourth cover 222, which is an upper cover placed on the opposite side of the bottom surface.

The docking station 200 may include a second connector 250 including a second connection terminal for signal transmission to the intraoral sensor 100 or power supply for charging.

Herein, the second connector 250 may be accommodated in the second casing 220, and may be configured such that an end of the second connector 250 is exposed through a second connector hole 225 formed in the second casing 220.

The second connector 250 is electrically connected to the corresponding first connector 150 of the intraoral sensor 100 to perform signal transmission or charging.

Here, in the embodiment, a magnetic force may be used to achieve stable connection between the first and second connectors 150 and 250.

In this regard, for example, one of the first and second connectors 150 and 250 may be provided with a magnet that generates a magnetic force, and the remaining one may be provided with a magnet or a magnetic body magnetized in a magnetic field, so that the first and second connectors 150 and 250 can be stably connected by the magnetic force.

Herein, a permanent magnet or an electromagnet may be used as the magnet used in the connector.

Further, the arrangement direction (or magnetic field direction) of the two magnetic poles (that is, N pole and S pole) used in one of the first and second connectors 150 and 250 may be configured to be parallel to the exposed surface of the corresponding connector (or the junction surface between the connectors). For example, the arrangement direction (or magnetic field direction) of the two magnetic poles (that is, N pole and S pole) used in one of the first and second connectors 150 and 250 may be placed on opposite sides of the corresponding connector along the exposed surface of the corresponding connector (or the junction surface between the connectors), and one of N pole and S pole may be located on the left side and the remaining one on the right side.

Meanwhile, in the case where a magnet is also used in the remaining one of the first and second connectors 150 and 250, the magnetic pole arrangement direction of a magnet of the first connector 150 (for example, N pole→S pole direction from left to right) and the magnetic pole arrangement direction of a magnet of the second connector 250 (for example, N pole→S pole direction from right to left) are preferably opposite to each other.

When the directionality of the magnetic pole is set as described above, the first and second connectors 150 and 250 can be properly connected by the magnetic force by eliminating the problem of erroneous connection between connection terminals of the first and second connectors 150 and 250.

Hereinafter, the structure of the intraoral sensor and the docking station according to the embodiment will be described in more detail with reference to FIGS. 6 to 9.

Figure 6:
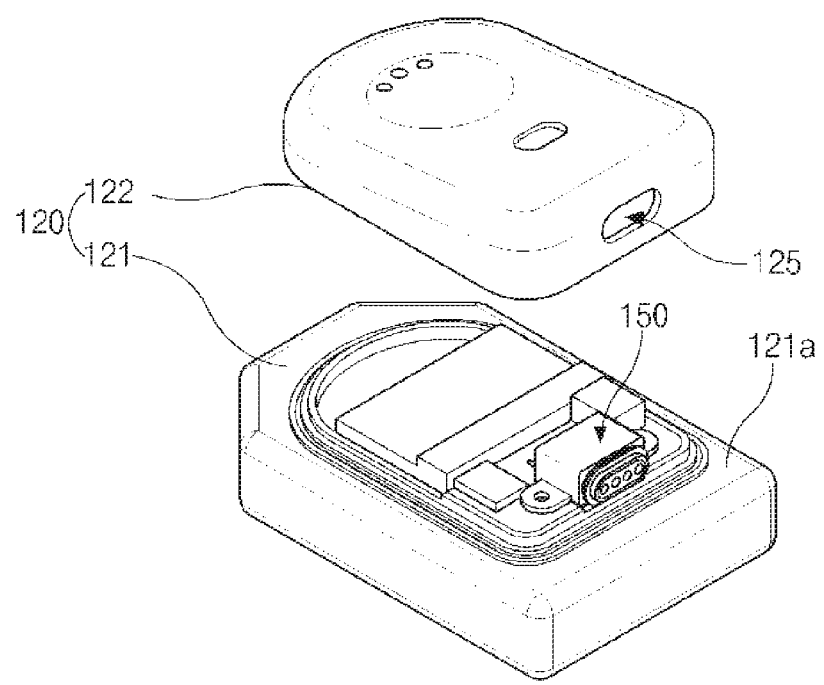
FIG. 6 is an exploded view showing the intraoral sensor according to the second embodiment of the present invention.
Figure 7:
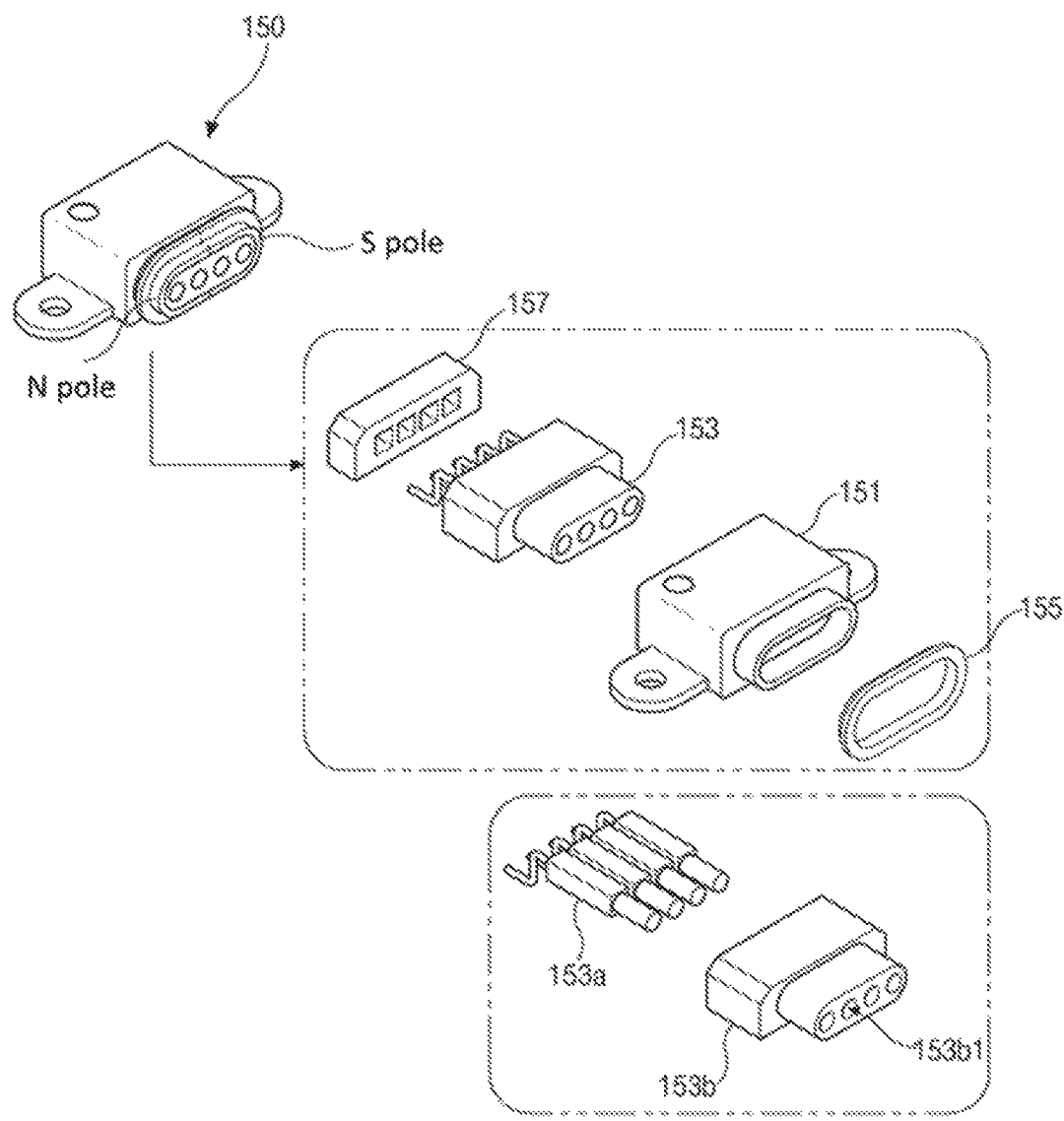
FIG. 7 is an exploded view showing a first connector of FIG. 6.
Figure 8:
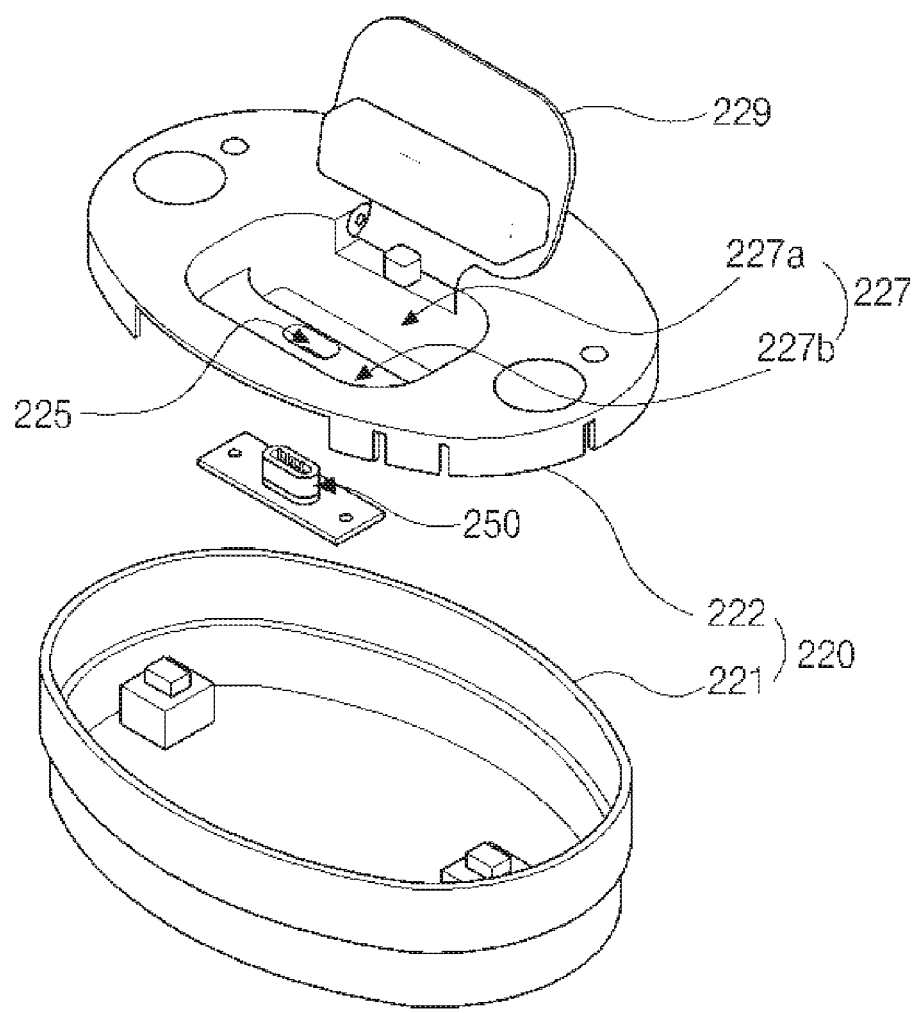
FIG. 8 is an exploded view showing a docking station according to the second embodiment of the present invention.
Figure 9:
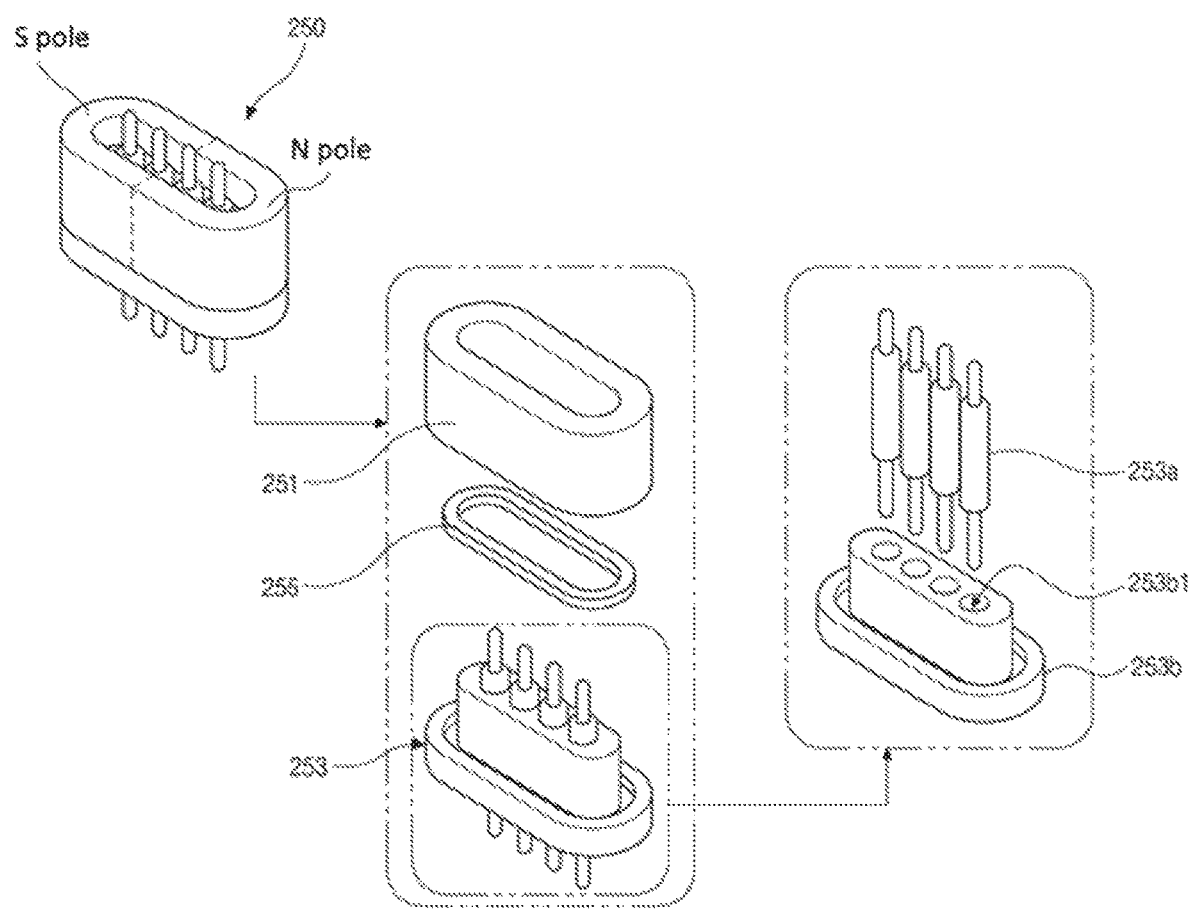
FIG. 9 is an exploded view showing a second connector of FIG. 8.

FIG. 6 is an exploded perspective view showing the intraoral sensor according to the second embodiment of the present invention, and FIG. 7 is an exploded perspective view showing a first connector of FIG. 6. FIG. 8 is an exploded perspective view showing a docking station according to the second embodiment of the present invention, and FIG. 9 is an exploded perspective view showing a second connector of FIG. 8.

Firstly, the intraoral sensor 100 may be provided with the first casing 120 configured to accommodate internal components, and the first casing 120 may include the first cover 121 and the second cover 122 disposed opposite to each other based on an incident direction, and coupled with each other.

Here, the second cover 122 may have a shape protruding in the incident direction, that is, a backward direction, and the first connector hole 125 may be formed on one side of the second cover 122 to expose the first connector 150. Herein, preferably, the first connector 150 is in a shape that is substantially not protruding out of the first connector hole 125, that is, in a non-protruding shape, but is not limited thereto. In this regard, when the first connector 150 is formed in a protruding shape, damage may occur in a process of coupling/separating the first connector 150 to and from the second connector 250, and thus the first connector is formed in a non-protruding shape, thereby preventing the first connector 150 from being damaged.

Further, the first cover 121 may have a shape protruding (or extending) in the outward direction to have a larger area than the second cover 122, and an outer edge portion 121a which is an outer protruding portion of the first cover 121 at the position where the first connector hole 125 is formed may be formed.

The first connector 150 may include a first housing 151 as a support body which defines the actual appearance thereof, and a first connection terminal module 153 inserted into the first housing 151.

Further, the first connector 150 may include: a ring-shaped first seal member 155 surrounding an outer circumferential surface of an upper portion, that is, a first end, of the first housing 151; and a second seal member 157 attached to a lower portion, that is, a second end of the first connection module 153 to provide a waterproof effect. Herein, the first seal member 155 may be formed of a material having elasticity such as silicone, but is not limited thereto. The second seal member 157 may be formed of a material such as epoxy, but is not limited thereto.

The first connection terminal module 153 may include a first mold 153b, and a plurality of pin-shaped first connection terminals 153a inserted into the first mold and configured such that an upper end thereof is exposed outside. In this regard, the first mold 153b may be formed with a plurality of holes 153b1 along a longitudinal direction thereof, and a part of the plurality of first connection terminals 153a is inserted into the corresponding holes 153b1 of first mold 153b, whereby an upper end thereof can be coupled through the holes 153b1 while being exposed without protruding outside (that is, outside on the upper side).

The first connector 150 configured as described above is assembled and is coupled to the first connector hole 125.

Next, the docking station 200 may be provided with the second casing 220 configured to accommodate internal components, and the second casing 220 may include the third cover 221 and the fourth cover 222 disposed opposite to each other based on the insertion direction (or mounting direction) of the intraoral sensor 100 and coupled with each other.

Here, the fourth cover 222 disposed at the top may be formed with a recessed groove 227 in which, when the intraoral sensor 100 is mounted, the first connector 150 as a part thereof is inserted thereinto. Further, the second connector hole 225 may be formed in the recessed groove 227 to expose the second connector 250. Meanwhile, a cover 229 covering the recessed groove 227 may be provided on the fourth cover 222. Herein, the recessed groove 227 is preferably formed to have a shape corresponding to the outer appearance of the lower portion of the intraoral sensor 100, which is inserted into the recessed groove. Accordingly, the recessed groove 227 may be formed to have a stepped structure, wherein the recessed groove 227 may be constituted by a first groove region 227a having a first depth into which the lower portion of the first cover 121 including the outer edge portion 121a is inserted, and a second groove region 227b having a second depth lower than the first depth into which the lower portion of the second cover 122 with the first connector 150 disposed therein is inserted.

Here, the second connector hole 225 with the second connector 250 disposed thereinto is formed in the second groove region 227b.

Preferably, the second connector 250 is in a shape that is substantially not protruding out of the second connector hole 225, that is, in a non-protruding shape, but is not limited thereto. In this regard, when the second connector 250 is formed in a protruding shape, damage may occur in a process of coupling/separating the first connector 150 to and from the second connector 250, and thus the second connector is formed in a non-protruding shape, thereby preventing the second connector 250 from being damaged.

The second connector 250 may include a second housing 251 as a support body which defines the actual appearance thereof, and a second connection terminal module 253, at least a part of which is inserted into the second housing 251.

Further, the second connector 250 may include a ring-shaped third seal member 255 inserted between the lower end of the second housing 251 and the outer edge of the second connection terminal module 253. Herein, the third seal member 255 may be formed of a material such as epoxy, but is not limited thereto.

The second connection terminal module 253 may include a second mold 253b, and a plurality of pin-shaped second connection terminals 253a inserted into the second mold and configured such that an upper end thereof protrudes outside. In this regard, the second mold 253b may be formed with a plurality of holes 253b1 along a longitudinal direction thereof, and a plurality of second connection terminals 253a is inserted into the corresponding holes 253b1 of the second mold 253b, whereby an upper end thereof can be coupled while being exposed by protruding outside (that is, outside on the upper side).

Herein, as the second connection terminals 253a, a cylinder-shaped pogo pin which can be adjusted in length with respect to an external force by showing elasticity and restoring force of the distal end part through an internal spring or the like may be used, but is not limited thereto. Further, the first and second connection terminals 153a and 253b may be opposite in shape, unlike the drawing.

The second connector 250 configured as described above is assembled and is coupled to the second connector hole 225.

Particularly, in the embodiment, one of the first housing 151 of the first connector 150 and the second housing 251 of the second connector 250 may be formed of a magnet that generates a magnetic force, and the remaining one may be formed of a magnet or a magnetic body magnetized in a magnetic field.

Herein, the arrangement direction (or magnetic field direction) of the two magnetic poles (that is, N pole and S pole) used in one of the first and second housings 151 and 251 may be configured to be parallel to the exposed surface of the corresponding connector (or the junction surface between the connectors). In other words, the arrangement direction of the two magnetic poles of the magnet may be perpendicular to a coupling direction of the first and second connectors 150 and 250. For example, the N pole and the S pole of the magnet may be disposed separately on the left and right sides of the corresponding housing.

Meanwhile, in the case where a magnet is also used in the remaining one of the first and second housings 151 and 251, the magnetic pole arrangement direction of a magnet of the first housing 151 and the magnetic pole arrangement direction of a magnet of the second housing 251 are preferably opposite to each other with the first and second housings 151 and 251 facing each other.

When the directionality of the magnetic pole is set as described above, the first and second connectors 150 and 250 can be properly connected by the magnetic force, and thereby, the problem of erroneous connection between the corresponding connection terminals 153a and 253a is eliminated, so that the first and second connectors 150 and 250 can be connected correctly.

Furthermore, since the docking station 200 is provided with the recessed groove 227 into which a lower portion of the intraoral sensor 100 is inserted when the intraoral sensor 100 is mounted, this mounting structure ensures the connection directionality of the first and second connectors 150 and 250 so that the connection stability between the first and second connectors 150 and 250 can be further improved.

Figure 10:
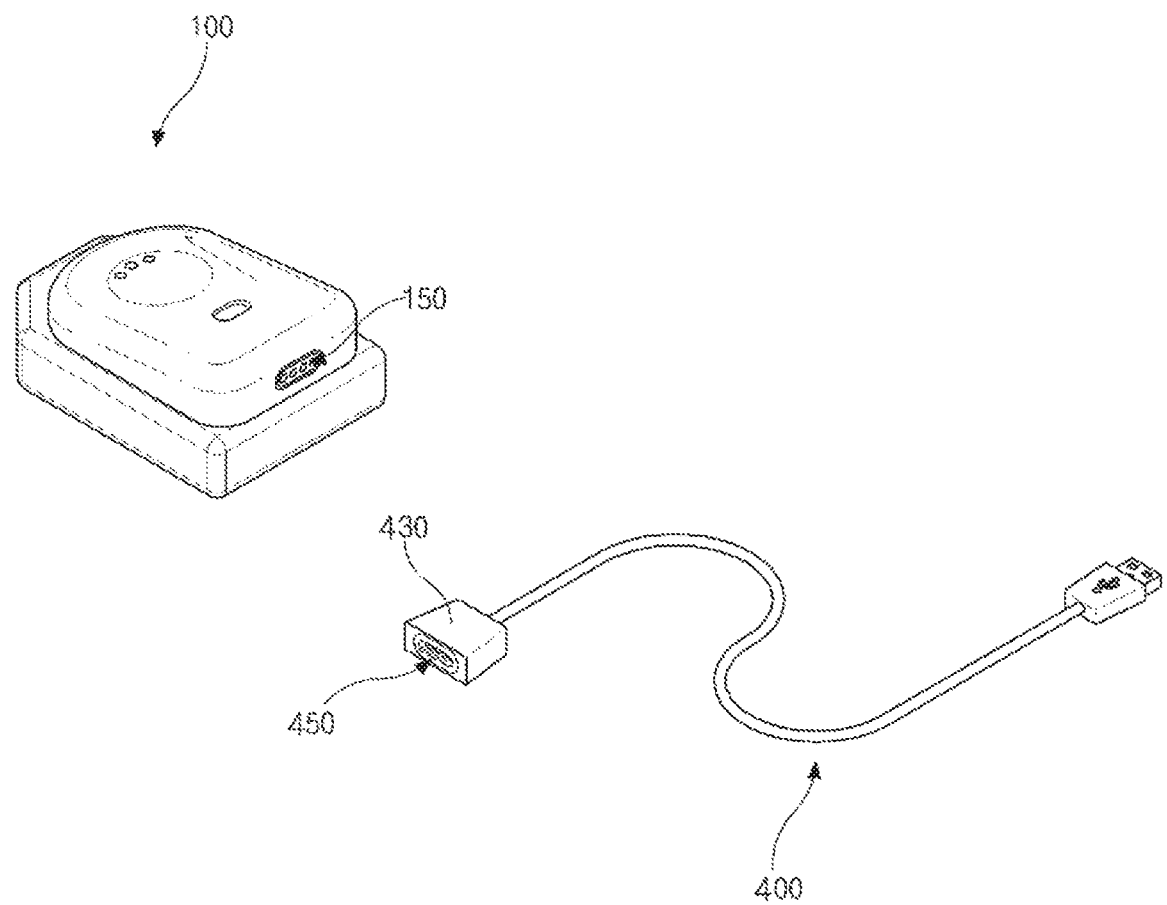
FIG. 10 is a view showing the intraoral sensor and a transmission cable detachably connected thereto according to the second embodiment of the present invention.

Meanwhile, the intraoral sensor 100 described above may be configured to be connected to the computer as needed via the detachable transmission cable, and reference can be made to FIG. 10 in this regard.

FIG. 10 is a view showing a use of a transmission cable detachably connected to the intraoral sensor according to the second embodiment of the present invention.

Referring to FIG. 10, an end of the transmission cable 400 is provided with a third connector 350 that is coupled to the first connector 150 of the intraoral sensor 100 and connected thereto.

Herein, the third connector 350 may be formed to have substantially the same structure as the second connector 250 provided in the docking station 200 of the first embodiment, and a detailed description of the third connector 350 may be omitted.

The third connector 350 is preferably formed in a non-protruding shape by being inserted into a connector casing 320 formed at an end of the transmission cable 400 not to be exposed outside, but is not limited thereto. As such, thanks to the non-protruding shape, it is possible to prevent the third connector 350 from being damaged.

The third connector 350 may be configured similar to the second connector 250 of the second embodiment, and may include a third housing as a support body which defines the actual appearance thereof, and a third connection terminal module, at least a part of which is inserted into the third housing.

Particularly, in the embodiment, one of the first housing of the first connector 150 and the third housing of the third connector 350 may be formed of a magnet that generates a magnetic force, and the remaining one may be formed of a magnet or a magnetic body magnetized in a magnetic field.

Herein, the arrangement direction (or magnetic field direction) of the two magnetic poles (that is, N pole and S pole) used in one of the first and third housings may be configured to be parallel to the exposed surface of the corresponding connector (or the junction surface between the connectors).

Meanwhile, in the case where a magnet is also used in the remaining one of the first and third housings, the magnetic pole arrangement direction of a magnet of the first housing and the magnetic pole arrangement direction of a magnet of the third housing are preferably opposite to each other with the first and third housings facing each other.

When the directionality of the magnetic pole is set as described above, the first and third connectors can be properly connected by the magnetic force, and thereby, the problem of erroneous connection between the corresponding connection terminals is eliminated, so that the first and third connectors can be connected correctly.

Particularly, in the case where the transmission cable 400 is used, the user frequently experiences difficulty in correctly coupling the transmission cable 400 to the intraoral sensor 100.

Accordingly, coupling between the connectors using magnetic force may be more effective when using the transmission cable 350 as in this embodiment.

As described above, in the X-ray imaging system according to the embodiment of the present invention, the cableless intraoral sensor provided with the battery and the memory therein may be used. Further, by using the docking station to which the intraoral sensor is docked, or the transmission cable detachably connected to the intraoral sensor, it is possible to transmit an image signal generated from the intraoral sensor to the computer.

As described above, by implementing the cableless intraoral sensor, the convenience of intraoral X-ray imaging can be maximized, and breakage of the transmission cable or connection failure can be fundamentally eliminated, whereby it is possible to effectively improve the limitation of intraoral X-ray imaging due to use of a conventional cable-type intraoral sensor.

Further, in connecting the intraoral sensor to the docking station or transmission cable, the corresponding connectors are connected by using magnetic force.

Thereby, the problem of erroneous connection between the connection terminals of the connectors is eliminated, thereby ensuring the connection stability between the connectors.

Although a preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. An intraoral sensor comprising:
a sensor panel configured to generate an image signal by X-ray imaging;
a circuit unit provided with a driver circuit configured to drive the sensor panel;
a memory configured to store the image signal;
a battery configured to supply driving power to the sensor panel and the circuit unit;
a casing configured to accommodate the sensor panel, the circuit unit, the memory, and the battery;
a sloped protrusion provided on a backside of the casing, wherein the sloped protrusion includes a first connector configured to include a signal transmission terminal to transmit and receive signals from a peripheral device; and
a detachable transmission cable having a horseshoe shaped coupler and a second connector at one end to be insert into the sloped protrusion, and the second connector to be connected to the first connector,
wherein the intraoral sensor transmits signals directly through the first connector or via the detachable transmission cable to the peripheral device.

2. The intraoral sensor of claim 1, wherein the first connector includes a magnet or a magnetic body.

3. An X-ray imaging system comprising:
an intraoral sensor, wherein the intraoral sensor comprises,
a sensor panel configured to generate an image signal by X-ray imaging,
a circuit unit provided with a driver circuit configured to drive the sensor panel,
a memory configured to store the image signal,
a battery configured to supply driving power to the sensor panel and the circuit unit,
a casing configured to accommodate the sensor panel, the circuit unit, the memory, and the battery,
a sloped protrusion provided on a backside of the casing, wherein the protrusion includes a first connector configured to include a signal transmission terminal to transmit the image signal and a power terminal to supply power to the battery;
a detachable transmission cable having a horseshoe shaped coupler and a second connector at one end to be insert into the sloped protrusion, and the second connector to be connected to the first connector; and
an intraoral docking station, the docking station includes a third connector configured to directly connect to the first connector of the intraoral sensor or connect to the intraoral sensor via the detachable transmission cable.

4. The X-ray imaging system of claim 3, wherein one of the first and second connectors includes a magnet.

5. The X-ray imaging system of claim 4, wherein the first and second connectors include respective magnets of which magnetic poles thereof are opposite to each other.

6. The X-ray imaging system of claim 3, wherein the docking station includes a memory configured to store the transmitted image signal and further configured to connect to an external computer.

7. The X-ray imaging system of claim 3, wherein an inner surface of the coupler is provided with a plurality of connection terminals connecting the first and third of connectors.

8. The X-ray imaging system of claim 3, wherein one of the first and third connectors includes a magnet.

9. The X-ray imaging system of claim 8, wherein the first and third connectors include respective magnets of which magnetic poles thereof are opposite to each other.

10. The intraoral sensor of claim 1, wherein the signal transmission terminal transmits the image signal to the peripheral device and supplies power to the battery.

11. The intraoral sensor of claim 1, wherein the peripheral device is a docketing station.

12. The intraoral sensor of claim 1, wherein the intraoral sensor with the transmission cable coupled thereto is inserted into an oral cavity.

13. The X-ray imaging system of claim 3, wherein the intraoral sensor with the transmission cable coupled thereto is inserted into an oral cavity.

14. The X-ray imaging system of claim 3, wherein the docking station further includes a display window implemented as a display panel and configured to display information on a state of the intraoral sensor, a transmission state of the image signal, a charging state of the battery, a capacity of the memory, a state of X-ray imaging operations of the intraoral sensor.

15. The X-ray imaging system of claim 3, wherein the docking station receives the image signal from the intraoral sensor and supplies power to the battery.

* * * * *